US012653681B2

(12) United States Patent
Liu et al.

(10) Patent No.: US 12,653,681 B2
(45) Date of Patent: Jun. 16, 2026

(54) METHOD FOR MANUFACTURING PERSONALIZED BIONIC ARTIFICIAL CERVICAL DISC PROSTHESIS AND PROSTHESIS

(71) Applicant: Beijing Tiantan Hospital, Capital Medical University, Beijing (CN)

(72) Inventors: Baoge Liu, Beijing (CN); Bingxuan Wu, Beijing (CN); Lin Lin, Beijing (CN); Dacheng Sang, Beijing (CN); Tianhua Rong, Beijing (CN)

(73) Assignee: BEIJING TIANTAN HOSPITAL, CAPITAL MEDICAL UNIVERSITY, Beijing (CN)

( * ) Notice: Subject to any disclaimer, the term of this patent is extended or adjusted under 35 U.S.C. 154(b) by 318 days.

(21) Appl. No.: 18/502,156

(22) Filed: Nov. 6, 2023

(65) Prior Publication Data
US 2024/0277480 A1 Aug. 22, 2024

(30) Foreign Application Priority Data
Feb. 16, 2023 (CN) .......................... 202310119670.4

(51) Int. Cl.
*A61F 2/30* (2006.01)
*A61F 2/44* (2006.01)
(Continued)

(52) U.S. Cl.
CPC .......... *A61F 2/3094* (2013.01); *A61F 2/4425* (2013.01); *A61L 27/14* (2013.01);
(Continued)

(58) Field of Classification Search
CPC ................ A61F 2/3094; A61F 2/30942; A61F 2002/30955; A61F 2/44; A61F 2/441;
(Continued)

(56) References Cited

U.S. PATENT DOCUMENTS 11,744,644 B2 * 9/2023 Wilkinson ........... A61B 17/157
606/88
2007/0050032 A1 * 3/2007 Gittings ................ A61F 2/4425
623/17.13
(Continued)

FOREIGN PATENT DOCUMENTS

CN 106901876 A 6/2017
CN 108095863 A 6/2018

OTHER PUBLICATIONS

Sang, D., et al., The Differences Among Kinematic Parameters for Evaluating the Quality of Intervertebral Motion of the Cervical Spine in Clinical and Experimental Studies: Concepts, Research and Measurement Techniques. A Literature Review, World Neurosurg. Jan. 2020:133:343-357.e1. doi: 10.1016/j.wneu.2019.09.075. Epub Sep. 21, 2019.
(Continued)

*Primary Examiner* — Eduardo C Robert
*Assistant Examiner* — Christina Negrellirodriguez
(74) *Attorney, Agent, or Firm* — Mark T. Vogelbacker; Eckert Seamans Cherin & Mellott, LLC

(57) ABSTRACT

A method for manufacturing a personalized bionic artificial cervical disc prosthesis and a prosthesis can include establishing a three-dimensional simulation model of a cervical spine with a degenerated cervical disc; modifying morphological structures and material properties of the degenerated cervical disc to obtain a three-dimensional simulation model of the artificial cervical disc prosthesis; implanting the three-dimensional simulation model of the artificial cervical disc prosthesis into the three-dimensional simulation model of the cervical spine, applying a load to the three-dimensional simulation model of the cervical spine to mimic physiological motion of the cervical spine, and calculating kinematics and biomechanical indexes of an implanted segment and adjacent segments; adjusting the three-dimen-
(Continued)

sional simulation model of the artificial cervical disc prosthesis until the abnormal ICR can be corrected and optimum biomechanical effects can be obtained after the prosthesis is implanted; and manufacturing the artificial cervical disc prosthesis.

6 Claims, 3 Drawing Sheets

(51) Int. Cl.
    A61L 27/14         (2006.01)
    A61L 27/52         (2006.01)
(52) U.S. Cl.
    CPC ..... *A61L 27/52* (2013.01); *A61F 2002/30943* (2013.01); *A61F 2002/30971* (2013.01); *A61F 2002/443* (2013.01); *A61F 2002/444* (2013.01); *A61F 2220/0016* (2013.01); *A61F 2240/002* (2013.01); *A61F 2310/00023* (2013.01); *A61F 2310/00407* (2013.01); *A61F 2310/00796* (2013.01)

(58) Field of Classification Search
    CPC .. A61F 2/442; A61F 2/4425; A61F 2002/443; A61F 2002/4435; A61F 2002/444; A61B 34/10
    USPC .......................... 623/17.11–17.16; 703/1, 11
    See application file for complete search history.

(56) References Cited

U.S. PATENT DOCUMENTS

| | | | |
|---|---|---|---|
| 2008/0103596 A1* | 5/2008 | Shikinami | A61F 2/442 |
| | | | 623/17.15 |
| 2011/0082552 A1* | 4/2011 | Wistrom | A61F 2/4425 |
| | | | 623/17.16 |
| 2016/0374820 A1* | 12/2016 | Khandaker | A61F 2/442 |
| | | | 623/17.12 |

OTHER PUBLICATIONS

Office Action of Mar. 31, 2023 issued in Chinese priroity application No. 202310119670.4.

* cited by examiner

METHOD FOR MANUFACTURING PERSONALIZED BIONIC ARTIFICIAL CERVICAL DISC PROSTHESIS AND PROSTHESIS

CROSS-REFERENCE TO RELATED APPLICATION

This patent application claims the benefit and priority of Chinese Patent Application No. 202310119670.4, filed on Feb. 16, 2023, the disclosure of which is incorporated by reference herein in its entirety as part of the present application.

TECHNICAL FIELD

The present disclosure relates to the technical field of medical devices, and in particular to a method for manufacturing a personalized bionic artificial cervical disc prosthesis and a prosthesis.

BACKGROUND

Anterior cervical discectomy and fusion (ACDF) has always been considered as the "golden standard" for the treatment of cervical degenerated diseases. However, after ACDF is performed, the range of motion (ROM) of the surgical segment is lost, the ROM of adjacent segments is increased, and the mechanical distribution is abnormal, leading to the increase of the risk of adjacent segment disease (ASD). Artificial cervical disc arthroplasty (CDA), as an alternative surgical procedure, can maintain the ROM of the surgical segment, avoid excessive load distribution of adjacent segments, mimic physiological motion patterns of cervical spine as much as possible, reduce the incidence of ASD, and obtain better clinical results. Since the Food and Drug Administration (FDA) first approved Presige-ST artificial cervical disc prosthesis in 2007, nine types of artificial cervical disc prostheses have been approved by FDA for marketing, which are Presige-ST (2007), ProDisc-C (2007), Bryan (2009), Secure-C (2012), PCM (2012), Mobi-C (2013), PrestigeLP (2014) and M6-C (2019) based on the approved time sequence. In addition, dozens of artificial cervical disc prostheses that have not been approved by FDA are undergoing clinical trials at different stages.

There are various types of artificial cervical disc prostheses, and motion patterns are provided according to the prostheses, that is, internal joints of the prosthesis can be divided into ball-socket joints (e.g., ProDisc-C), ball-trough joints (e.g., PrestigeLP), sliding nucleus pulposus (e.g., Mobi-C) and closed nucleus pulposus (e.g., Bryan). These motion modes have significant differences in the design of the Center of rotation (COR) of the cervical disc prostheses. The COR of prosthesis with the sliding nucleus pulposus is constantly changed during flexion and extension motion and lateral bending motion, so as to mimic the COR of normal cervical disc. The prosthesis with the ball-socket joint has a fixed COR, which forces the prosthesis to move in a predetermined pattern. The COR of prosthesis with the ball-socket joint is similar to that of the prosthesis with the sliding nucleus pulposus which has some translational motion, but is mainly a rotational motion. The prosthesis with closed nucleus pulposus is closest to the normal cervical disc in biomechanical properties which has the possibility to reconstruct normal ICR trajectory and couple motion. Early cervical disc products only mechanically mimic motion patterns of the cervical disc in six degrees of freedom, while the prosthesis with the closed nucleus pulposus marks the advent of the highly bionic era of cervical disc prostheses, which is the main direction of development in the future.

According to the limitation of artificial cervical disc prostheses on six degrees of freedom of motion, the prostheses can be divided into a constrained prosthesis (e.g., ProDisc-C), a semi-constrained prosthesis (e.g., Mobi-C) and a non-restrictive prosthesis (e.g., Bryan). The constrained prosthesis only provides intervertebral rotation, but constrains axial compression and translation, which forces cervical spine to move along a COR position of prosthesis after the prosthesis is implanted, leading to the lack of the ability to restore the intervertebral physiological motion pattern, and the increase of the risk of ASD. The non-restrictive prosthesis has a full six degrees of freedom of motion, i.e., rotational and translational motion in all three axial planes, so as to maximally mimic physiologic motion, but also have drawbacks such as excessive motion and increased stress loads on adjacent segments. The semi-constrained prosthesis is between constrained and non-restrictive prostheses, but cannot fully mimic the physiologic motion pattern.

The design of the material of artificial cervical disc prosthesis plays an important role in cervical kinematics, biomechanics, safety and effectiveness. The material of artificial cervical disc prosthesis should be biocompatible, chemically inert, non-toxic and non-carcinogenic. Since the CDA surgery is suitable for patients with mild or moderate cervical degeneration, and there is an obvious trend of rejuvenation of patients, the material must be wear-resistant, corrosion-resistant and have good fatigue strength, and the elasticity modulus of the material endplate should be as close as possible to bone tissue, so as to avoid the "stress shielding" effect. Moreover, the internal material of the prosthesis should be as close as possible to properties of the physiological cervical disc material, so as to mimic the physiological motion pattern.

The artificial cervical disc prosthesis has been developed for more than half a century, and its effectiveness and safety have been widely proven, but there are still some complications after CDA is performed, such as postoperative neck pain, abnormal alignment, prosthesis subsidence, heterotopic ossification. Biochemical abnormality caused by the situation that existing prostheses cannot effectively correct abnormal ICR (instantaneous center of rotation) and restore physiological motion pattern is one of the important reasons for the above complications of prostheses. In addition, the design data and prosthesis specifications of artificial cervical disc prosthesis used in China refer to anatomical characteristics of European and American people, which are not completely matched with the cervical anatomical parameters of Chinese. Moreover, the mass-produced cervical disc prostheses with fixed specification are not suitable for all patients with cervical spondylosis. The prosthesis endplate does not completely cover and is closely connected to the vertebral endplate, which is not conducive to the uniform transmission of mechanical load; and the vertebral bone endplate needs to be polished, which increases the risk of prosthesis subsidence.

SUMMARY

An objective of the present disclosure is to provide a method for manufacturing a personalized bionic artificial cervical disc prosthesis, and a prosthesis, so as to solve the problems existing in the prior art and to obtain an artificial cervical disc prosthesis which is highly matched with cervical anatomical parameters of a patient. Meanwhile, the obtained artificial cervical disc prosthesis also has the ability to correct abnormal ICR, can reconstruct physiological motion pattern, mimic the physiological motion of normal cervical spine, and obtain more balanced biomechanical effect.

To achieve the objective above, the present disclosure provides the following solutions: a method for manufacturing a personalized bionic artificial cervical disc prosthesis is provided, including following steps:

S1: establishing a three-dimensional simulation model of a cervical spine with a degenerated cervical disc;

S2: modifying morphological structures and material properties of the degenerated cervical disc in the three-dimensional simulation model of the cervical spine to obtain a three-dimensional simulation model of the artificial cervical disc prosthesis;

S3: implanting the three-dimensional simulation model of the artificial cervical disc prosthesis into the three-dimensional simulation model of the cervical spine, applying a load to the three-dimensional simulation model of cervical spine to mimic physiologic motion of the cervical spine, and calculating kinematics and biomechanical indexes of an implanted segment and adjacent segments, wherein obtained kinematics parameters include an instantaneous center of rotation;

S4: adjusting the three-dimensional simulation model of the artificial cervical disc prosthesis according to results of the calculating until the indexes reaches a standard; and S5: manufacturing the artificial cervical disc prosthesis according to the three-dimensional simulation model of the artificial cervical disc prosthesis.

Preferably, in S2, a height and an endplate curvature of the artificial cervical disc prosthesis are increased according to degeneration degree of the cervical disc, and the material properties of the cervical disc are modified to obtain the three-dimensional simulation model of the artificial cervical disc prosthesis.

Preferably, in S3, prior to implanting the three-dimensional simulation model of the artificial cervical disc prosthesis into the three-dimensional simulation model of the cervical spine, osteophytes at vertebral anterior border are removed, and after implanting the three-dimensional simulation model of the artificial cervical disc prosthesis into the three-dimensional simulation model of the cervical spine, motion of the three-dimensional simulation model of the cervical spine is analyzed by means of finite element analysis software, wherein, a vertebral inferior endplate at a bottom is fixed, and a load is applied to a vertebral superior endplate at a top, and the kinematics and biomechanical indexes of the implanted segment and adjacent segments are obtained by taking range of motion of normal cervical spine segment as a boundary condition during a process of analyzation.

Preferably, in S3, in flexion and extension motion of the cervical spine, motion of the whole cervical spine is regarded as a circular arc with a fixed center, wherein a center point with zero velocity exists in the circular arc, and the center point is a center of rotation. In the flexion and extension motion of the cervical spine, motion at each time in the whole motion of the cervical spine is regarded as a circular arc with a fixed center with zero velocity. A trajectory conjoined by centers is the instantaneous center of rotation, which is a trajectory formed by a series of centers of rotation.

Preferably, in S1, CT data of the cervical spine with the degenerated cervical disc of a patient with cervical spondylosis is imported into medical image control software for image segmentation, and then a physical structure is derived, the physical structure is imported into forward engineering software for smooth and symmetrical processing; a cervical geometric model is reconstructed by means of reverse engineering software, and mesh division is conducted on the cervical geometric model in finite element pre-processing software to form the three-dimensional simulation model of the cervical spine with the degenerated cervical disc.

Preferably, in S2, the three-dimensional simulation model of the artificial cervical disc prosthesis is provided with an annulus fibrosus prosthesis with Young's modulus from 2 MPa to 4 MPa, a nucleus pulposus prosthesis with Young's modulus of 1 MPa, a superior endplate and an inferior endplate each of which has Young's modulus of 114,000 Mpa, and Poisson's ratio of 0.35 V. In S3, the obtained biomechanical parameters include a displacement-moment curve, facet joint stress, bone-implant interface stress, an intradiscal pressure, and stress on prosthesis core.

The present disclosure further provides a personalized bionic artificial cervical disc prosthesis, including a superior endplate, an inferior endplate, and an intermediate elasticity complex connected between the superior endplate and the inferior endplate. Each of the superior endplate and the inferior endplate is provided with a plurality of inverted teeth for penetrating into a vertebral endplate, and the intermediate elasticity complex comprises a nucleus pulposus prosthesis and an annulus fibrosus prosthesis in an annular shape. The nucleus pulposus prosthesis is located in a middle of the annulus fibrosus prosthesis and is in fit with an inner ring wall in an annular shape of the annulus fibrosus prosthesis.

Preferably, the superior endplate and the inferior endplate are made of titanium alloy, and a surface of each of the superior endplate and the inferior endplate is coated with a titanium hydroxyapatite coating.

Preferably, the annulus fibrosus prosthesis is made of a polyurethane material, and the nucleus pulposus prosthesis is made of a hydrogel material.

Preferably, the inverted tooth is in a shape of a quadrangular pyramid.

Compared with the prior art, the present disclosure has the following technical effects:

1. According to the method for manufacturing the personalized bionic artificial disc prosthesis in the present disclosure, personalized design can be conducted according to different degeneration conditions of cervical discs of different patients, so as to obtain cervical disc prostheses highly matched with cervical anatomical parameters of the patients.

2. In the finite element simulation process, the ICR data of the three-dimensional simulation model are obtained and then compared with that of the existing prosthesis and a normal cervical disc, and the height and the endplate curvature of the prosthesis are constantly modified, such that the endplate curvature of the LBG-disc-C prosthesis completely conforms to the anatomical data of the patients, the method do not destroy the vertebral bone endplate, and is completely fits with the vertebral bone endplate, which is more conducive to the uniform transmission of mechanical load, can reduce bone-implant interface stress, and reduce the risk of prosthesis subsidence. The final cervical disc prosthesis also has the ability to correct abnormal ICR, restore physiological motion pattern, mimic normal cervical physiological motion, and obtain more balanced biomechanical effect.

3. In the LBGdisc-C prosthesis of the present disclosure, the material properties and motion generation mode (through elastic composite deformation) of the elasticity complex are similar to those of physiological cervical disc, thus maintaining the ROM of the implanted segment without increasing the load of adjacent segments and reducing the risk of ASD.

BRIEF DESCRIPTION OF THE DRAWINGS

To describe the technical solutions in the embodiments of the present disclosure or in the prior art more clearly, the following briefly introduces the accompanying drawings required for describing the embodiments. Apparently, the accompanying drawings in the following description show merely some embodiments of the present disclosure, and those of ordinary skill in the art may still derive other drawings from these accompanying drawings without creative efforts.

Figure 1:
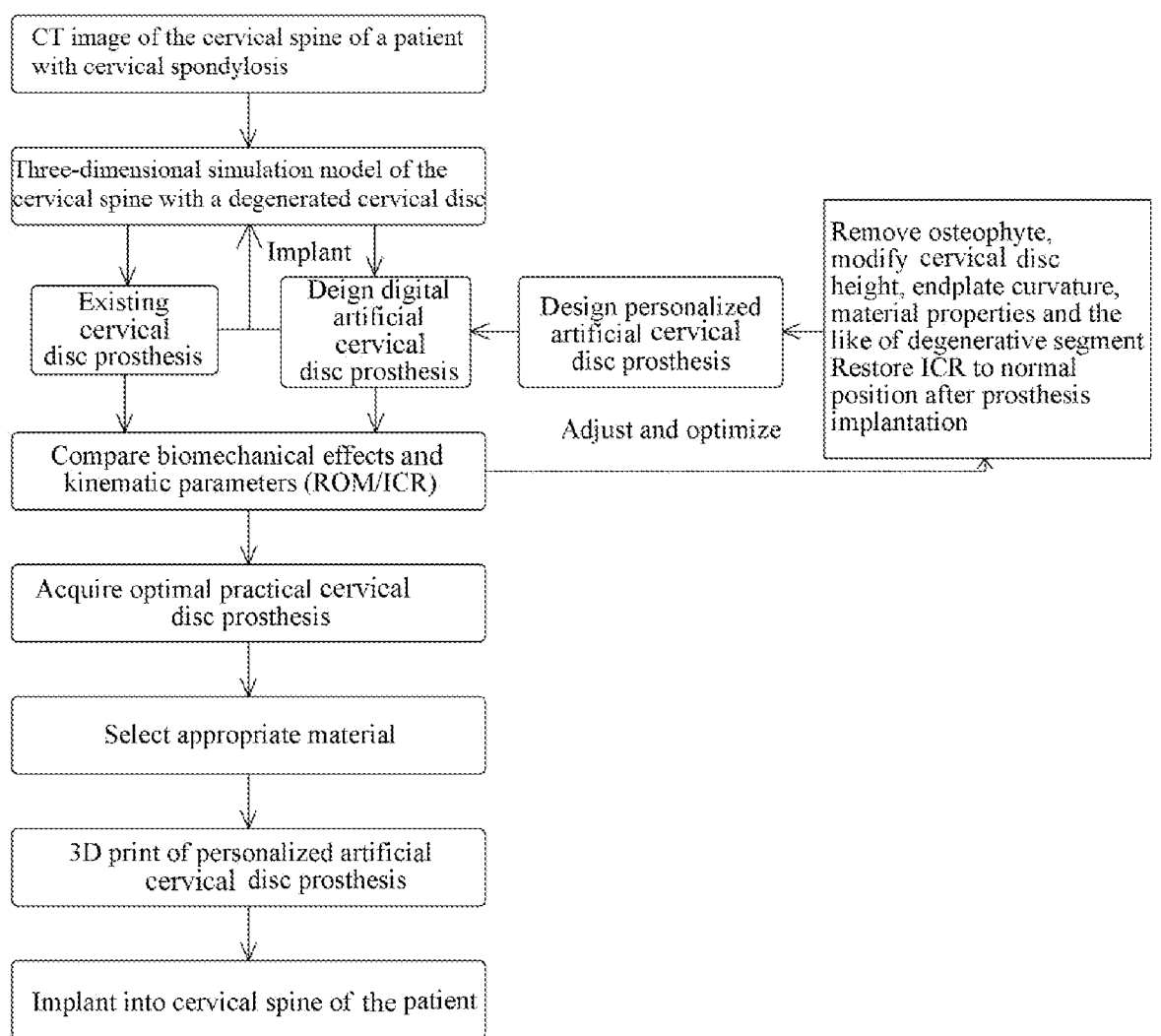
FIG. 1 is flow chart of a method for manufacturing a personalized bionic artificial cervical disc prosthesis.

In the drawings: 1—superior endplate; 2—inferior endplate; 3—nucleus pulposus prosthesis; 4—annulus fibrosus prosthesis; and 5—inverted tooth.

DETAILED DESCRIPTION OF THE EMBODIMENTS

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by a person of ordinary skill in the art based on the embodiments of the present disclosure without creative efforts shall fall within the scope of the present disclosure.

An objective of the present disclosure is to provide a method for manufacturing a personalized bionic artificial cervical disc prosthesis, and a prosthesis, so as to solve the problems existing in the prior art and to obtain a cervical disc prosthesis which is highly matched with cervical anatomical parameters of a patient. At the same time, the obtained cervical disc prosthesis also has the ability to correct abnormal ICR, can reconstruct physiological motion pattern, mimic the physiological motion of normal cervical spine, and obtain more balanced biomechanical effect.

To make the objectives, features and advantages of the present disclosure more apparently and understandably, the following further describes the present disclosure in detail with reference to the accompanying drawings and the specific embodiments.

Embodiment I

Because the mass-produced cervical disc prostheses with fixed specification in the prior art are not suitable for all patients with cervical spondylosis, the method for manufacturing a personalized bionic artificial cervical disc prosthesis (LBGdisc-C prosthesis) provided by this embodiment adopts the reverse idea to design a personalized bionic artificial cervical disc prosthesis (named LBGdisc-C) which conforms to the anatomical characteristics of Chinese people based on the change law of the instantaneous center of rotation which is the key kinematic parameter and introduces its personalized production process. The cervical disc prosthesis can achieve the purpose of correcting abnormal ICR, reconstructing physiological motion pattern and uniformly transmitting mechanical load while maintaining the ROM of the implanted segment and reducing the mechanical load of adjacent segments, so as to reduce the complications after cervical disc arthroplasty is performed and improve the postoperative clinical effects. The method for manufacturing a personalized bionic artificial cervical disc prosthesis mainly includes the following steps 1-4:

In Step 1: Based on the concept of personalized design of this embodiment, a three-dimensional simulation model of a cervical spine after the cervical disc is degenerated is established firstly, which lays a foundation for subsequent design and prosthesis shape adjustment. Specifically, CT data of a patient with cervical spondylosis are imported into medical image control software (Mimics 10.0; Material Technologies, Leuven, Belgium) for image segmentation, and then a physical structure is derived. The physical structure is imported into forward engineering software 3-Matic for smoothing and symmetry treatment, and then a cervical spine geometric model is reconstructed by means of the reverse engineering software (Geomagic studio 10.0; Geomagic Inc., North Carolina, USA) and mesh division is conducted in finite element preprocessing software (Hypermesh 11.0; Altair Engineering Corp, Michigan, USA) to form a three-dimensional simulation model of a cervical spine.

In Step 2: The degenerated cervical disc model in the three-dimensional simulation model of a cervical spine is corrected based on a vertebral model and a degenerated cervical disc model in the three-dimensional simulation model of a cervical spine obtained in Step S1, thus obtaining a three-dimensional simulation model of a cervical disc prosthesis to replace the degenerated cervical disc. Specifically, according to previous studies, the degenerated cervical disc decreases the intervertebral height, forms the osteophyte at vertebral anterior border, changes the endplate curvature and hardens the endplate in morphology. Meanwhile, results in the aging of cervical disc cells, dehydration of nucleus pulposus, the change of cervical disc material properties. The change of morphology and material property of cervical disc subjected to degeneration are important reasons for ICR abnormality. Therefore, in order to mimic the normal cervical disc, correct abnormal ICR and restore the physiological motion pattern, it is necessary to remove osteophytes at the vertebral anterior border, restore the intervertebral height to a normal range, increase the endplate curvature and restore the cervical disc to normal material properties. In above operation, the removal of the osteophytes at the vertebral anterior border and the restoration of the cervical disc to normal material properties do not need to be adjusted according to the anatomical structure of the patient, since osteophytes at the vertebral anterior border need to be completely removed, and the normal material properties are fixed values (Table 1) which do not need to be changed. The intervertebral height and endplate curvature should be modified according to the degeneration degree and anatomical structure of the patient. When the cervical disc is in slight degeneration, the intervertebral height is decreased by less than 25%. When the cervical disc is in moderate degeneration, the intervertebral height is decreased by 25-50%. When the cervical disc in severe degeneration, it is not suitable for performing the artificial cervical disc prosthesis arthroplasty which is not within the scope of design. In the degenerated cervical disc prosthesis, the endplate curvature decreases with the increase of degeneration degree, so that the endplate tends to be flat. Therefore, according to the degeneration degree of each patient, the height of LBGdisc-C prosthesis is appropriately increased, and the endplate curvature is appropriately increased. In the whole design process of the prosthesis, the width and depth of LBGdisc-C prosthesis remain unchanged, which is always the width and depth of the intervertebral space of the patient, so as to ensure that the endplate of the LBGdisc-C prosthesis is in fully fit with the vertebral endplate, and the larger the surface area of the endplate of the LBGdisc-C prosthesis, the more favorable the uniform transmission of loads. However, the existing endplate of prosthesis is generally smaller than the vertebral endplate, and the curvature of the endplate of prosthesis is not completely consistent with the endplate curvature, resulting that the endplate of prosthesis cannot be fully fit with the vertebral endplate, and the load transmission is concentrated in the smaller endplate of prosthesis, which increases the bone-implant interface stress, increases the risk of prosthesis subsidence and accelerates the wear of the endplate of prosthesis. The LBGdisc-C prosthesis in this embodiment can effectively avoid the above problems because the endplate area is retained to the greatest extent and then the endplate is in full fit with the vertebral endplate.

TABLE 1

Material properties and mesh types in the normal model

| Structure | Young's Modulus (MPa) | Poisson's Ratio (v) | Mesh type | Mesh numbers |
|---|---|---|---|---|
| Cortical bone | 10000 | 0.3 | Hexahedron | 3008 |
| Cancellous bone | 450 | 0.29 | Hexahedron and tetrahedron | 187004 |
| Cartilage endplate | 5 | 0.4 | Hexahedron | 4160 |
| Posterior structure | 3500 | 0.25 | Hexahedron and tetrahedron | 359138 |
| Annulus fibrosus matrix | 2 | 0.45 | Hexahedron | 2400 |
| Annulus fibrosus fiber | 110 | 0.3 | Pure tension truss | 3200 |
| Nucleus pulposus | 1 | 0.49 | Hexahedron | 5920 |
| Joint capsule Ligament | 10 | 0.4 | Hexahedron | 4068 |
| Anterior longitudinal ligament | Nonlinear | — | Connecting element | 20 |
| Posterior longitudinal ligament | Nonlinear | — | Connecting element | 20 |
| Ligamentum flavum | Nonlinear | — | Connecting element | 24 |

TABLE 1-continued

Material properties and mesh types in the normal model

| Structure | Young's Modulus (MPa) | Poisson's Ratio (v) | Mesh type | Mesh numbers |
|---|---|---|---|---|
| Interspinous ligament | Nonlinear | — | Connecting element | 20 |
| Capsular ligament | Nonlinear | — | Connecting element | 64 |

In Step 3: The cervical disc prosthesis obtained in Step 2 is an initially corrected cervical disc prosthesis of which kinematics and biomechanical properties are not enough to reach the level of normal cervical disc. Therefore, parameters of the initially corrected cervical disc prosthesis need to be verified and modified to obtain an cervical disc prosthesis that has good kinematics and biomechanical properties and is really suitable for patients. Specifically, the three-dimensional simulation model of the cervical disc prosthesis is implanted into the three-dimensional simulation model of the cervical spine after the cervical disc is degenerated, loads are applied to the three-dimensional simulation model of cervical spine to mimic physiological motion thereof, and kinematics and biomechanical indexes of an implanted segment and adjacent segments are calculated, wherein the obtained kinematics parameters include an instantaneous center of rotation. The obtained parameters are compared with those of the normal model and the existing prosthesis model, if the parameters obtained after the LBGdisc-C prosthesis is implanted have no remarkable advantages in comparison with the existing prosthesis model, or the abnormal ICR cannot be corrected, the height and the endplate curvature of the prosthesis are continuously corrected until optimal parameters are obtained. At this time, the size of the LBGdisc-C prosthesis is most suitable for the patient.

Load application and boundary conditions: the inferior endplate 2 of the lowest vertebrae in each model is fixed, and a pure torque of 1 Nm and a follow-up load of 73.6 N are applied to the superior endplate 1 of the uppermost vertebrae in the normal model, the motion of cervical spine in six directions including forward flexion and backward extension, left and right lateral flexion, left and right rotation is mimicked. According to a displacement control loading criterion, the ROM obtained in the normal model is taken as a boundary condition of the degeneration model and all the artificial cervical disc prosthesis arthroplasty models, that is, the load is applied to move the degeneration model and all the artificial disc prosthesis arthroplasty models to the same position as the normal model.

Kinematics parameters are as follows: Range of motion (ROM), Instantaneous center of rotation (ICR).

Biomechanical parameters are as follows: Displacement-moment curves, Facet joint stress, Bone-implant interface stress, Intradiscal pressure, and Stress on prosthesis core.

The meaning of center of rotation (COR) is that in flexion and extension motion, the motion of the whole cervical spine is regarded as a circular arc with a fixed center, and there is a center point with zero velocity in this circular arc. This fixed center point is COR. The meaning of Instantaneous center of rotation (ICR) is that in the flexion and extension motion, the motion of cervical spine at each time during the whole motion is regarded as a circular arc, and each circular arc has a fixed center with zero velocity. A trajectory conjoined by these centers is ICR. COR and ICR are both parameters describing the quality of intervertebral motion (i.e., motion pattern), and ICR is a trajectory composed of a series of COR, which can dynamically describe the motion process. The above concepts have been described in detail in "The Differences Among Kinematic Parameters for Evaluating the Quality of Intervertebral Motion of the Cervical Spine in Clinical and Experimental Studies Concepts, Research and Measurement Technologies", and are concepts known to those skilled in the art.

In Step 4: A cervical disc prosthesis is manufactured by means of 3D printing technology according to the three-dimensional simulation model of the cervical disc prosthesis.

The 3D printing technology is well known to those skilled in the art, and the specific 3D printing process of the cervical disc prosthesis is not described in detail in this embodiment.

According to the method for manufacturing a personalized bionic artificial cervical disc prosthesis in this embodiment, personalized design can be conducted according to different degeneration conditions of cervical discs of different patients, so as to obtain cervical disc prostheses highly matched with cervical anatomical parameters of the patients. In the finite element simulation process, the ICR data of the three-dimensional simulation model are obtained and then compared with that of the existing prosthesis and a normal cervical disc, and the height and the endplate curvature of the prosthesis are constantly modified, such that the endplate curvature of the LBGdisc-C prosthesis completely conforms to the anatomical data of the patients, the method do not destroy the vertebral bone endplate, and is completely fits with the vertebral bone endplate, which is more conducive to the uniform transmission of mechanical load, can reduce bone-implant interface stress, and reduce the risk of prosthesis subsidence. The final cervical disc prosthesis also has the ability to correct abnormal ICR, restore physiological motion pattern, mimic normal cervical physiological motion, and obtain more balanced biomechanical effect.

Embodiment II

Figure 2:
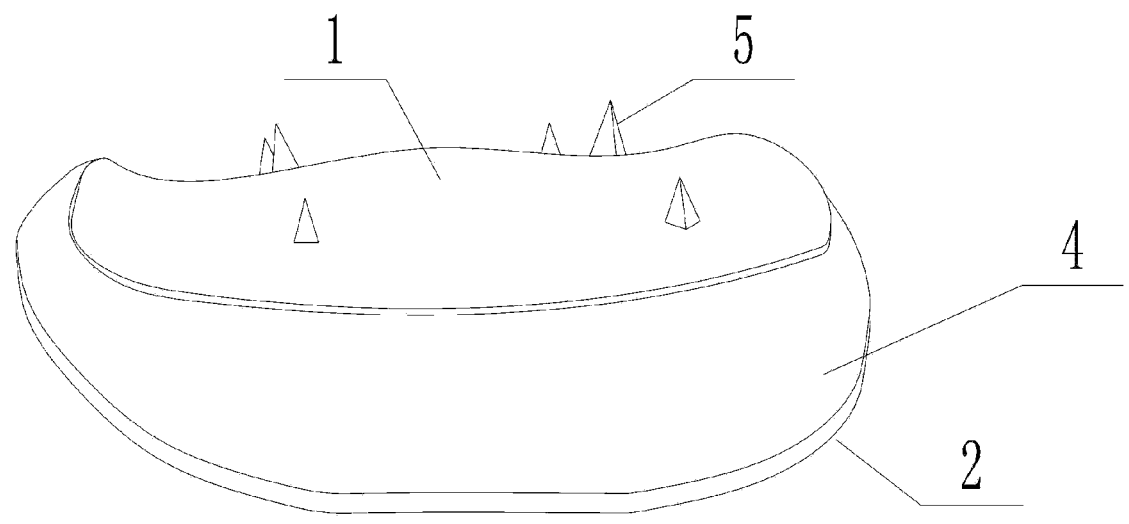
FIG. 2 is a front view of a cervical disc prosthesis in accordance with the present disclosure.
Figure 3:
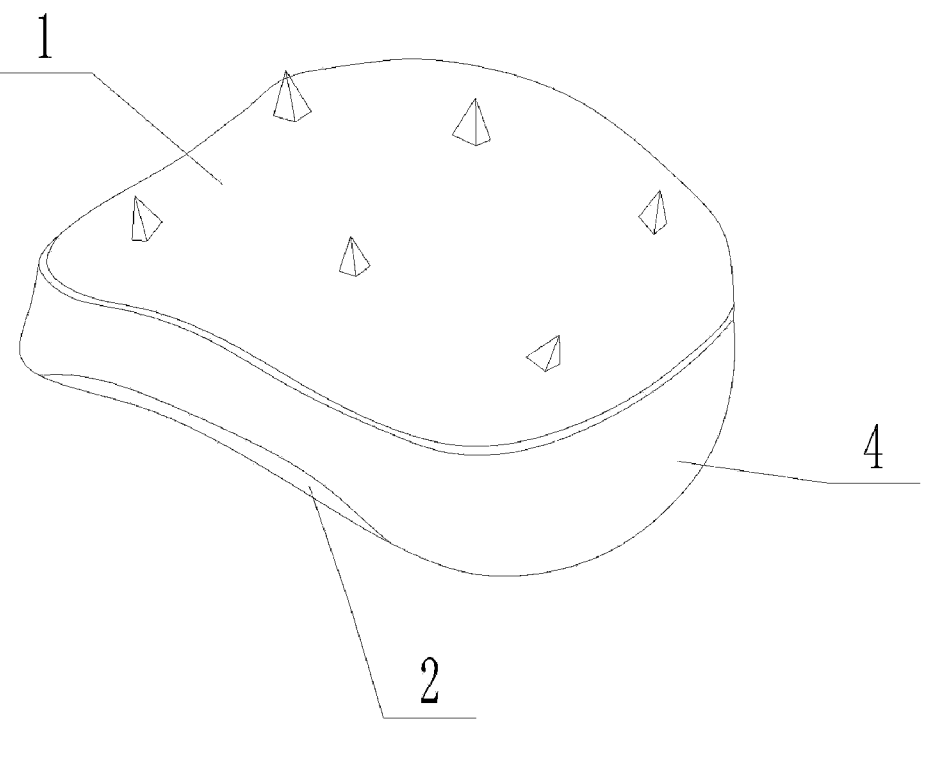
FIG. 3 is an isometric view of the cervical disc prosthesis.
Figure 4:
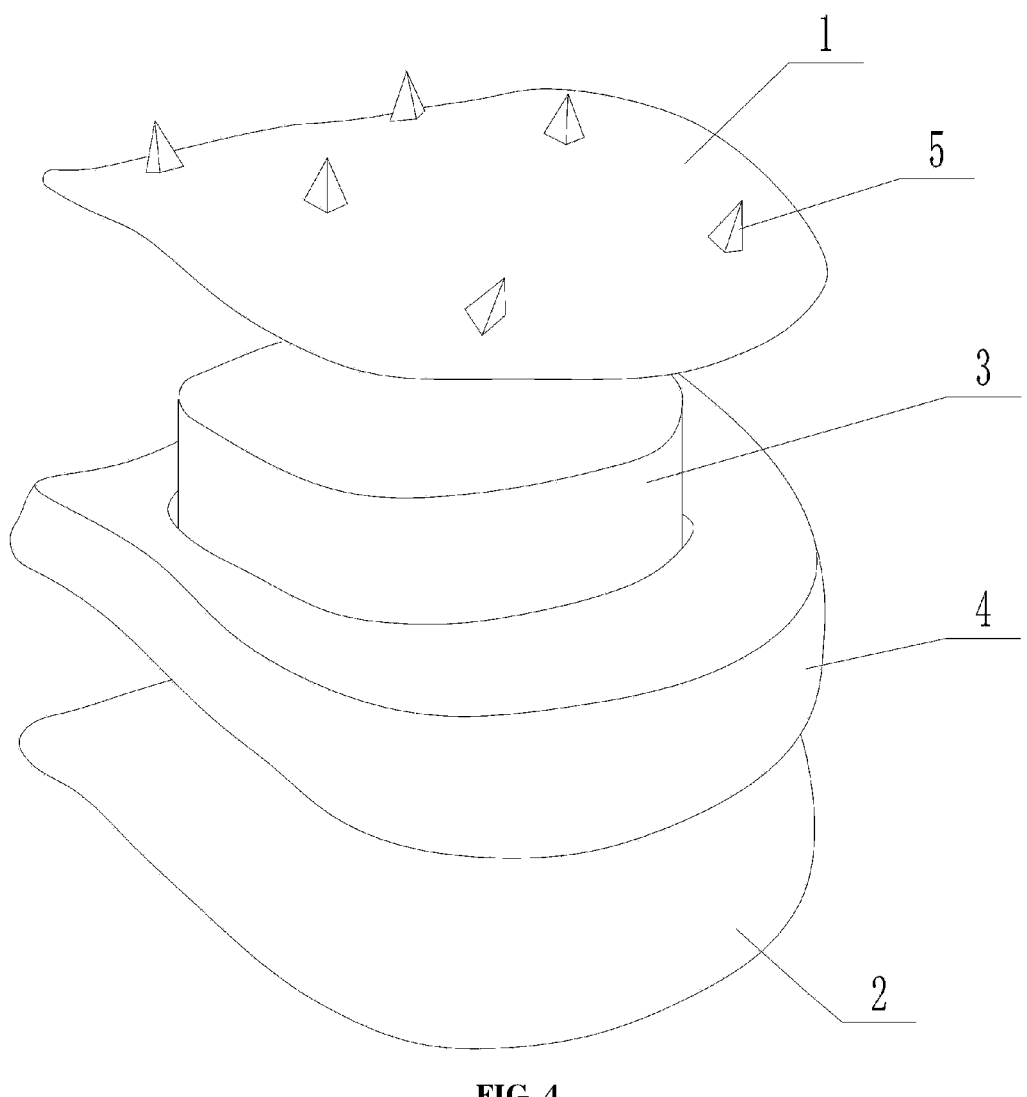
FIG. 4 is a disassembly view of the cervical disc prosthesis.

As shown in FIG. 2 to FIG. 4, a personalized bionic artificial cervical disc prosthesis is provided according to this embodiment, including a superior endplate 1, an inferior endplate 2, and an intermediate elasticity complex connected between the superior endplate 1 and the inferior endplate 2. Each of the superior endplate 1 and the inferior endplate 2 is provided with six inverted teeth 5 for penetrating into a vertebral endplate, and the inverted tooth 5 is in the shape of a quadrangular pyramid. The intermediate elasticity complex includes a nucleus pulposus prosthesis 3 and an annular fibrosus prosthesis 4 in an annular shape. The nucleus pulposus prosthesis 3 is located in the middle of the annulus fibrosus prosthesis 4 and in fit with an inner ring wall in an annular shape.

Both the superior endplate 1 and the inferior endplate 2 are made of titanium alloy, preferably an improved titanium alloy material. Due to the titanium alloy has the elastic modulus that is less than that of cobalt-chromium-molybdenum alloy and has the magnetic resonance compatibility, the titanium alloy is an ideal orthopedic implant material. However, the titanium alloy has the defects of non-wear resistance, easy oxidation and low hardness. The improved titanium alloy material, such as Ti-6Al-4V, not only has the elastic modulus closer to that of cortical bone, but also has better mechanical properties and biocompatibility.

In order to promote bone growth and then achieve synostosis at the interface between prosthesis and vertebrae, bioactive and osteoinductive materials are commonly used to prepare coatings on the surface of endplate of a prosthesis. The endplate of the LBGdisc-C prosthesis is intended to be coated with a titanium hydroxyapatite coating which has good biocompatibility and osteoinductivity, and is an ideal surface coating material. Therefore, the surfaces of the upper endplate 1 and the lower endplate 2 in this embodiment are both coated with titanium hydroxyapatite coatings.

The annulus fibrous prosthesis 4 is made of a polyurethane material, and the nucleus pulposus prosthesis 3 is made of a hydrogel material. The intermediate elasticity complex of the LBGdisc-C prosthesis is a high molecular polymer, which is composed of an outer annulus fibrous-like polymer (polyurethane material with Young's modulus from 2 MPa to 4 MPa) and an inner nucleus pulposus polymer (hydrogel with Young's modulus of 1 MPa), and the material properties (Young's modulus, Poisson's ratio) and size of the intermediate elasticity complex are the same as those of normal cervical disc tissue.

In the LBGdisc-C prosthesis of this embodiment, the material properties and motion generation mode (through elasticity complex deformation) of elasticity complex are similar to those of the physiological cervical disc, which can maintain the ROM of implanted segments without increasing the load of adjacent segments, and reduce the risk of ASD.

Adaptive changes conducted according to actual needs are within the scope of the present disclosure.

It should be noted that: for those skilled in the art, apparently, the present disclosure is not limited to details of the exemplary embodiments, and may be expressed in other specific forms without departing from the spirit or basic characteristics of the present disclosure. Therefore, in any way, the embodiments should be regarded as exemplary, not limitative; and the scope of the present disclosure is limited by the appended claims, instead of the above description. Thus, all variations intended to fall into the meaning and scope of equivalent elements of the claims should be covered within the present disclosure. Any reference numerals in the claims shall not be regarded as limitations to the concerned claims.

What is claimed is:

1. A method for manufacturing a personalized bionic artificial cervical disc prosthesis, comprising following steps:

S1: establishing a three-dimensional simulation model of a cervical spine with a degenerated cervical disc;

S2: modifying morphological structures and material properties of the degenerated cervical disc in the three-dimensional simulation model of the cervical spine to obtain a three-dimensional simulation model of the artificial cervical disc prosthesis;

S3: implanting the three-dimensional simulation model of the artificial cervical disc prosthesis into the three-dimensional simulation model of the cervical spine, applying a load to the three-dimensional simulation model of the cervical spine to mimic physiologic motion of the cervical spine, and calculating kinematics indexes and biomechanical indexes of an implanted segment and adjacent segments, wherein the calculated kinematics indexes comprise an instantaneous center of rotation;

S4: adjusting the three-dimensional simulation model of the artificial cervical disc prosthesis according to results of the calculated kinematics indexes and the calculated biomechanical indexes until the calculated kinematics indexes and the calculated biomechanical indexes reach a standard; and S5: manufacturing the artificial cervical disc prosthesis according to the three-dimensional simulation model of the artificial cervical disc prosthesis.

2. The method for manufacturing a personalized bionic artificial cervical disc prosthesis according to claim 1, wherein in S2, a height and an endplate curvature of the artificial cervical disc prosthesis are increased according to degeneration degree of the cervical disc, and the material properties of the cervical disc are modified to obtain the three-dimensional simulation model of the artificial cervical disc prosthesis.

3. The method for manufacturing a personalized bionic artificial cervical disc prosthesis according to claim 2, wherein in S3, prior to implanting the three-dimensional simulation model of the artificial cervical disc prosthesis into the three-dimensional simulation model of the cervical spine, osteophytes at a vertebral anterior border are removed, and after implanting the three-dimensional simulation model of the artificial cervical disc prosthesis into the three-dimensional simulation model of the cervical spine, motion of the three-dimensional simulation model of the cervical spine is analyzed by means of finite element analysis software, wherein a vertebral inferior endplate at a bottom is fixed, and a load is applied to a vertebral superior endplate at a top, and the kinematics indexes and the biomechanical indexes of the implanted segment and adjacent segments are calculated by taking a range of motion of a normal cervical spine segment as a boundary condition during a process of analyzation.

4. The method for manufacturing a personalized bionic artificial cervical disc prosthesis according to claim 3, wherein in S3, in a flexion-extension motion of the cervical spine, motion of the cervical spine is regarded as a circular arc with a fixed center, wherein a center point with zero velocity exists in the circular arc, and the center point is a center of rotation; in the flexion-extension motion of the cervical spine, motion at each time in a whole motion of the cervical spine is regarded as a circular arc with a fixed center with zero velocity; and a trajectory conjoined by centers is the instantaneous center of rotation, which is a trajectory formed by a series of centers of rotation.

5. The method for manufacturing a personalized bionic artificial cervical disc prosthesis according to claim 4, wherein in S1, CT data of the cervical spine with the degenerated cervical disc of a patient with cervical spondylosis is imported into medical image control software for image segmentation and then a physical structure is derived; the physical structure is imported into forward engineering software for smooth and symmetrical processing; a cervical geometric model is reconstructed by means of reverse engineering software, and mesh division is conducted on the cervical geometric model in finite element pre-processing software to form the three-dimensional simulation model of the cervical spine with the degenerated cervical disc.

6. The method for manufacturing a personalized bionic artificial cervical disc prosthesis according to claim 5, wherein in S2, the three-dimensional simulation model of the artificial cervical disc prosthesis is provided with an annulus fibrosus prosthesis with Young's modulus from 2 MPa to 4 MPa, a nucleus pulposus prosthesis with Young's modulus of 1 MPa, a superior endplate and an inferior endplate each of which has Young's modulus of 114,000 MPa, and Poisson's ratio of 0.35 V; in S3, the calculated biomechanical indexes comprise a displacement-moment curve, facet joint stress, bone-implant interface stress, an intradiscal pressure, and stress on prosthesis core.

* * * * *